United States Patent
Vaez-Iravani et al.

(10) Patent No.: US 7,295,303 B1
(45) Date of Patent: Nov. 13, 2007

(54) METHODS AND APPARATUS FOR INSPECTING A SAMPLE

(75) Inventors: Mehdi Vaez-Iravani, Los Gatos, CA (US); Guoheng Zhao, Milpitas, CA (US)

(73) Assignee: Kla-Tencor Technologies Corporation, Milpitas, CA (US)

( * ) Notice: Subject to any disclaimer, the term of this patent is extended or adjusted under 35 U.S.C. 154(b) by 504 days.

(21) Appl. No.: 11/013,976

(22) Filed: Dec. 14, 2004

Related U.S. Application Data (60) Provisional application No. 60/556,607, filed on Mar. 25, 2004.

(51) Int. Cl.
 *G01N 21/00* (2006.01)
(52) U.S. Cl. .............................. 356/237.4; 356/237.1; 356/237.5
(58) Field of Classification Search ...................... None
 See application file for complete search history.

(56) References Cited

U.S. PATENT DOCUMENTS

| | | | |
|---|---|---|---|
| 5,177,559 A * | 1/1993 | Batchelder et al. | ...... 356/237.5 |
| 6,885,446 B2 * | 4/2005 | Machavariani et al. | ..... 356/319 |
| 6,924,893 B2 * | 8/2005 | Oldenbourg et al. | ........ 356/369 |
| 7,041,998 B2 * | 5/2006 | Weiss et al. | ............. 356/237.4 |

OTHER PUBLICATIONS

U.S. Appl. No. 11/015,852, filed Dec. 15, 2004.

* cited by examiner

*Primary Examiner*—G. Lauchman
*Assistant Examiner*—Juan D Valentin
(74) *Attorney, Agent, or Firm*—Beyer Weaver LLP (57) ABSTRACT

Disclosed are methods and apparatus for inspecting or imaging a sample, such as a semiconductor wafer or reticle. In general, an optical inspection or microscopy tool that has a complex Fourier filter positioned in the Fourier plane of the radiation beam output from the sample in response to an incident beam striking the sample is provided. Use of such Fourier filter is also disclosed. In one implementation, the complex Fourier is designed to alter a phase, and possibly amplitude, of the scattered spatial portions of the output beam relative to the specular spatial portions of the output beam so as to enhance the contrast between the two. In another implementation, the complex Fourier serves to filter the effects of repeating structures on the sample from the output beam. The complex Fourier filter is used in conjunction with a complementary illumination aperture.

42 Claims, 8 Drawing Sheets

METHODS AND APPARATUS FOR INSPECTING A SAMPLE

CROSS REFERENCE TO RELATED PATENT APPLICATION

This application claims priority of U.S. Provisional Patent Application No. 60/556,607, entitled METHODS AND APPARATUS FOR INSPECTING A SAMPLE, filed 25 Mar. 2004 by Mehdi Vaez-Iravani, et al., which application is incorporated herein by reference in its entirety for all purposes.

BACKGROUND OF THE INVENTION

This invention pertains to apparatus and methods for inspecting a sample, such as a semiconductor wafer or photomask, using an optical inspection system. It also pertains to apparatus and methods for enhancing the detection of defects in such optical inspection systems.

Generally, the industry of semiconductor manufacturing involves highly complex techniques for fabricating integrating circuits using semiconductor materials. Due to the large scale of circuit integration and the decreasing size of semiconductor devices, decreasingly small defects, such as a particle, can cause the devices to fail. Defect inspection procedures are therefore critical to maintain quality control. Since the inspection procedures are an integral and significant part of the manufacturing process, the semiconductor industry is constantly seeking more accurate and efficient testing procedures.

Various inspection systems are used within the semiconductor industry to detect defects on a semiconductor device or wafer. One type of inspection tool is an optical inspection system. In optical inspection systems, one or more radiation beams are directed towards the semiconductor wafer and a reflected and/or scattered beam is then detected. The detected beam is used to then generate a detected electrical signal or an image, and such signal or image is then analyzed to determine whether defects are present on the wafer.

In certain applications, it is also frequently required that the inspection system have configurable illumination and imaging designs. The illumination and imaging configuration will be set to optimize the capture of different characteristics of defects or defect types. That is, different illumination and imaging configurations are more suitable for different types of defect inspections. Two broad categories of inspection configurations include bright field and dark field inspection. In general, the illumination and collection beam profiles are adjusted to achieve different inspection modes. In other words, different portions or angles of the incident or collection beam are blocked or transmitted.

For a dark field inspection, a portion of the illumination beam profile is typically blocked so that only a portion of the available illumination, for example a ring of illumination, is passed through to the wafer. A corresponding portion of the collection beam profile is then blocked so that only scattered light is collected. That is, blocked portions of the illumination beam correspond to unblocked portions of the collection beam, while unblocked portions of the illumination beam correspond to blocked portions of the collection beam. Both the illumination and the collection adjustments implement binary masks. That is, portions of the beam are totally blocked by the mask, while other portions of the beam pass unimpeded through the mask. Although these mask or aperture techniques have proved to be effective in many applications, they have limited sensitivity enhancement with respect to low contrast structures on the wafer, such as high aspect ratio vias.

In light of the foregoing, improved mechanisms for inspecting a sample are needed to achieve higher sensitivity for low contrast structures and defects and, accordingly to facilitate defect detection.

SUMMARY OF THE INVENTION

Accordingly, the present invention provides methods and apparatus for inspecting or imaging a sample, such as a semiconductor wafer or reticle. In general, an optical inspection or microscopy tool that has a complex Fourier filter which is positioned in the Fourier plane of the radiation beam output from the sample in response to an incident beam striking the sample is provided. Use of such Fourier filter is also disclosed. In one implementation, the complex Fourier is designed to alter a phase of the scattered spatial portions of the output beam relative to the specular spatial portions of the output beam so as to enhance the contrast between the two. In a further implementation, the Fourier filter is designed to alter both a phase and an amplitude of the scattered spatial portions of the output beam so as to contrast with the specular spatial portions of the output beam. In another implementation, the complex Fourier filter serves to eliminate the effects of repeating structures on the sample from the output beam. The complex Fourier filter is used in conjunction with a complementary illumination aperture.

In one embodiment, an apparatus for inspecting or imaging a semiconductor sample is disclosed. The apparatus generally includes an illumination lens arrangement for directing an incident beam towards a sample and an illumination aperture that includes at least a first area and a second area. The first area is arranged to block a blocked spatial portion of the incident beam and the second area is arranged to transmit a transmitted spatial portion of the incident beam towards the sample. The apparatus also includes an output lens arrangement for directing an output beam from the sample towards a detector, the output beam comprising a specular portion and a scattered light portion and a complex Fourier filter positioned within a Fourier plane of the sample. The complex Fourier filter has at least a first area and a second area that vary in material composition and/or thickness, and the relative material compositions and thickness of the first and second area are selected so as to alter a phase of the specular portions of the output beam relative to the scattered portions of the output beam so as to enhance contrast between the scattered and specular light portions of the output beam. In a further aspect, the relative material compositions and thickness of the first and second area are further selected so as to alter an amplitude (in addition to the phase) of the specular portions of the output beam relative to the scattered portions of the output beam so as to enhance contrast between the scattered and specular light portions of the output beam.

In a specific aspect, the first area of the complex Fourier filter corresponds to the first area of the illumination aperture and the second area of the complex Fourier filter corresponds to the second area of the illumination aperture. In a further aspect, the first area of the complex Fourier filter corresponds to scattered portions of the output beam and the second area of the complex Fourier filter corresponds to specular portions of the output beam. Alternatively, the first area of the complex Fourier filter corresponds to specular portions of the output beam and the second area of the complex Fourier filter corresponds to scattered portions of the output beam.

In a specific implementation, the first area of the complex Fourier filter is formed from a transparent substrate having a first thickness and the second area of the complex Fourier filter is formed from a thin film and the transparent substrate. The second area has a second thickness which differs from the first thickness. In a particular embodiment, the first area of the complex Fourier filter is formed from a step in the transparent substrate. In one aspect, the step height is also selected so as to alter a phase of the specular portions of the output beam relative to the scattered portions of the output beam so as to enhance contrast between the scattered and specular light portions of the output beam.

In an alternative embodiment, the first area of the complex Fourier filter is formed from a trench in the transparent substrate. In one aspect, the thin film is positioned within the trench of the first area. In another aspect, the thin film is positioned underneath the trench of the first area, implanted within the transparent substrate. In yet another aspect, the thin film is positioned on a surface of the transparent substrate that is opposite a surface of the transparent substrate that forms the trench of the first area.

In a specific implementation, the thin film is a dielectric material having a thickness and a composition which allows a corresponding portion of the output beam to pass there through with an altered phase. In another embodiment, the thin film is implanted in a portion of the transparent substrate. Alternatively, the thin film is deposited on a portion of the transparent substrate. In one embodiment, the transparent substrate is formed from a glass or a fused silica material In a specific implementation, the first area of the illumination aperture includes an inner opaque circular portion that blocks an inner circular portion of the incident beam; the second area of the illumination aperture being a transparent ring that surrounds the inner opaque circular portion and transmits a ring portion of the incident beam; the first area of the complex Fourier filter includes an inner transparent circular portion that transmits an inner circular portion of the output beam; and the second area of the complex Fourier filter includes a thin film ring that surrounds the inner transparent portion of the complex Fourier filter and changes a phase of a ring portion of the output beam, wherein the complex Fourier filter is positioned so that the some of the scattered light portions of the output beam pass through the inner transparent circular portion and the specular light portions are filtered through the thin film ring of the complex Fourier filter.

In a further embodiment, the first area of the illumination aperture further includes an outer opaque ring that surrounds the transparent ring and blocks an outer ring portion of the incident beam, and the first area of the complex Fourier filter further including an outer transparent ring that surrounds the thin film ring of the complex Fourier filter and transmits an outer ring portion of the incident beam, wherein the complex Fourier filter is positioned so that some of the scattered light portions of the output beam pass through the outer transparent ring of the complex Fourier filter. In one aspect, the thin film ring of the complex Fourier filter has a different thickness than the other portions of the inner transparent portion and the outer transparent portion of the complex Fourier filter. In a further aspect, the second area of the illumination aperture further includes a second transparent ring adjacent to the outer opaque ring and the first area of the illumination aperture further includes a second outer opaque ring adjacent to the second transparent ring. The second area of the complex Fourier filter further includes a second thin film ring that has the same thickness as the first thin film, and the second thin film is adjacent to the outer transparent ring and the first area of the complex Fourier filter further including a second transparent ring adjacent to the second thin film ring.

In another implementation, the second area of the illumination aperture includes a slit shaped opaque portion that blocks a slit shaped portion of the incident beam; the first area of the illumination aperture being a transparent portion that surrounds the slit shaped opaque portion of the illumination aperture and transmits a corresponding portion of the incident beam; the second area of the complex Fourier filter includes thin film slit shaped portion that transmits a slit shaped portion of the output beam and changes a phase of a slit shaped portion of the output beam; and the first area of the complex Fourier filter includes a transparent portion that surrounds the thin film slit portion and transmits a corresponding portion of the output beam, wherein the complex Fourier filter is positioned so that the some of the scattered light portions of the output beam pass through the transparent portion and the specular light portions are filtered through the thin film slit portion of the complex Fourier filter.

In yet another implementation, the second area of the illumination aperture includes an arc shaped opaque portion that blocks an arc shaped portion of the incident beam; the first area of the illumination aperture includes a transparent portion that surrounds the arc shaped opaque portion of the illumination aperture and transmits a corresponding portion of the incident beam; the second area of the complex Fourier filter includes a thin film arc shaped portion that transmits an arc shaped of the output beam and changes a phase of the arc shaped of the output beam; and the first area of the complex Fourier filter includes a transparent portion that surrounds the arc shaped portion and transmits a corresponding portion of the output beam, wherein the complex Fourier filter is positioned so that the some of the scattered light portions of the output beam pass through the transparent portion and the specular light portions are filtered through the arc shaped portion of the complex Fourier filter.

In one aspect, the output beam is transmitted through the sample. In another aspect, the output beam is both reflected from and transmitted through the sample. In yet another aspect, the output beam is both reflected and scattered from the sample. In a specific implementation, the illumination aperture is in the form of a plurality of illumination sources which are configurable to be selectively directed onto a first plurality of ends of a plurality optical fibers that are arranged to output the incident beam in the form of a plurality of incident beams from a second plurality of ends of the fibers. The fibers are coupled with a fiber modulator which is operable to substantially eliminate the speckle noise of the incident beams. In another aspect, the illumination lens arrangement and the output lens arrangement are both movable so as to adjust the complex Fourier filter dimensions.

In an alternative embodiment, an apparatus for inspecting a semiconductor sample having repeating structures is disclosed. The apparatus includes an illumination lens arrangement for directing an incident beam towards a sample and an illumination mask that include at least a plurality of first areas surrounded by at least a second area. The first areas are arranged to transmit a plurality of blocked illumination spatial portion of the incident beam and the second area is arranged to block a transmitted spatial portion of the incident beam towards the sample. The apparatus also includes an output lens arrangement for directing an output beam from the sample towards a detector. The output beam generally includes a specular portion and a scattered light portion. The apparatus further includes a complex Fourier mask positioned within a Fourier plane of the sample, wherein the complex Fourier mask has at least a plurality of first areas that are transparent and a second area that surrounds the first areas and is opaque. The first and second area positions are selected so as to filter portions of the output beam corresponding to repeating structures on the sample. The first areas of the complex Fourier filter correspond to the first areas of the illumination aperture and the second area of the complex Fourier filter corresponds to the second area of the illumination aperture.

In a further aspect, the illumination mask and the complex Fourier filter are integrated into a beam splitter that forms part of both the illumination lens arrangement and the output lens arrangement, and the beam splitter has a reflective portion and a transmissive portion. The reflective portion corresponds to the first areas of the illumination mask and the first areas of the complex Fourier filter and the transmissive portion corresponds to the second area of the illumination mask and the second area of the complex Fourier filter.

In another aspect, at least a portion of the output lens arrangement and the complex Fourier filter are movable so as to allow adjustment of the complex Fourier filter's dimensions. In a further embodiment, the illumination lens arrangement includes a group of movable mirrors so as to keep a conjugate image of the illumination mask constant during movement of the at least a portion of the output lens arrangement and the complex Fourier filter.

In a specific implementation, the first areas of the illumination aperture are a plurality of slits, and the first areas of the complex Fourier filter are a plurality of opaque slit portions. In another implementation, the first areas of the illumination aperture are an array of transparent portions and the second area of the illumination aperture is an opaque portion, and the first areas of the complex Fourier filter are an array of opaque portions and the second area of the complex Fourier filter is a transparent portion. In another implementation, the first areas of the illumination aperture are a checkerboards pattern of transparent portions and the second area of the illumination aperture is an opaque portion, and the first areas of the complex Fourier filter are a checkerboards pattern of opaque portions and the second area of the complex Fourier filter is a transparent portion.

These and other features and advantages of the present invention will be presented in more detail in the following specification of the invention and the accompanying figures which illustrate by way of example the principles of the invention.

DETAILED DESCRIPTION OF SPECIFIC EMBODIMENTS

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Low contrast defects and their surrounding area tend to have a slightly different refractive index than an identical area having no defect, and this difference in refractive index sometimes fails to cause a significant change in the light that is scattered from the sample, as compared with the reflected/specular light. Since the change in scattered light is relatively small, the contrast between a particular defect area and a defect free area may be undetectable with conventional optical inspection systems.

The optical systems of the present invention include a complex Fourier filter that is applied to the radiation beam that is output (e.g., scattered or reflected) from a sample in response to an incident radiation beam. In one embodiment, the complex Fourier filter is designed to change the phase (and possibly amplitude) of particular spatial portions of the output beam relative to other spatial portions of the output beam. In one application, the complex Fourier filter may be designed to enhance contrast as further described below. In one enhancement example, the difference in phase (and possibly amplitude) of light scattered from a defect area, such as residue in a high aspect ratio via or trench, and light reflected by other defect-free areas, such as a defect-free high aspect ratio via or trench, is amplified so as to enhance the contrast. In other embodiments, the complex Fourier filter may also be used for other suitable purposes, such as filtering repetitive structures from the detected light.

A complex Fourier filter may be implemented in any suitable manner. Although several embodiments of a complex Fourier filter are described further below, these examples are not meant to limit the scope of the invention. Additionally, although the complex Fourier filters are described as being implemented in specific semiconductor inspection systems, of course, these inspection system examples are merely exemplary. The inspection apparatus of the present invention are especially suitable for inspecting semiconductor devices or wafers, as well as reticles or masks. Other types of samples which may be inspected or imaged using the inspection apparatus of the present invention include any surface, such as a flat panel display. The Fourier filter may also be implemented in any suitable type of microscopy system.

In the inspection systems described herein, any suitable lens arrangement may generally be used to direct the incident beams towards the sample and direct the output beams emanating from the sample towards a detector. The output beams may be reflected or scattered from the sample or transmitted through the sample. Likewise, any suitable detector type or number of detection elements may be used to receive the output beams and provide an image or a signal based on the characteristics (e.g., intensity) of the received output beams.

Figure 1:
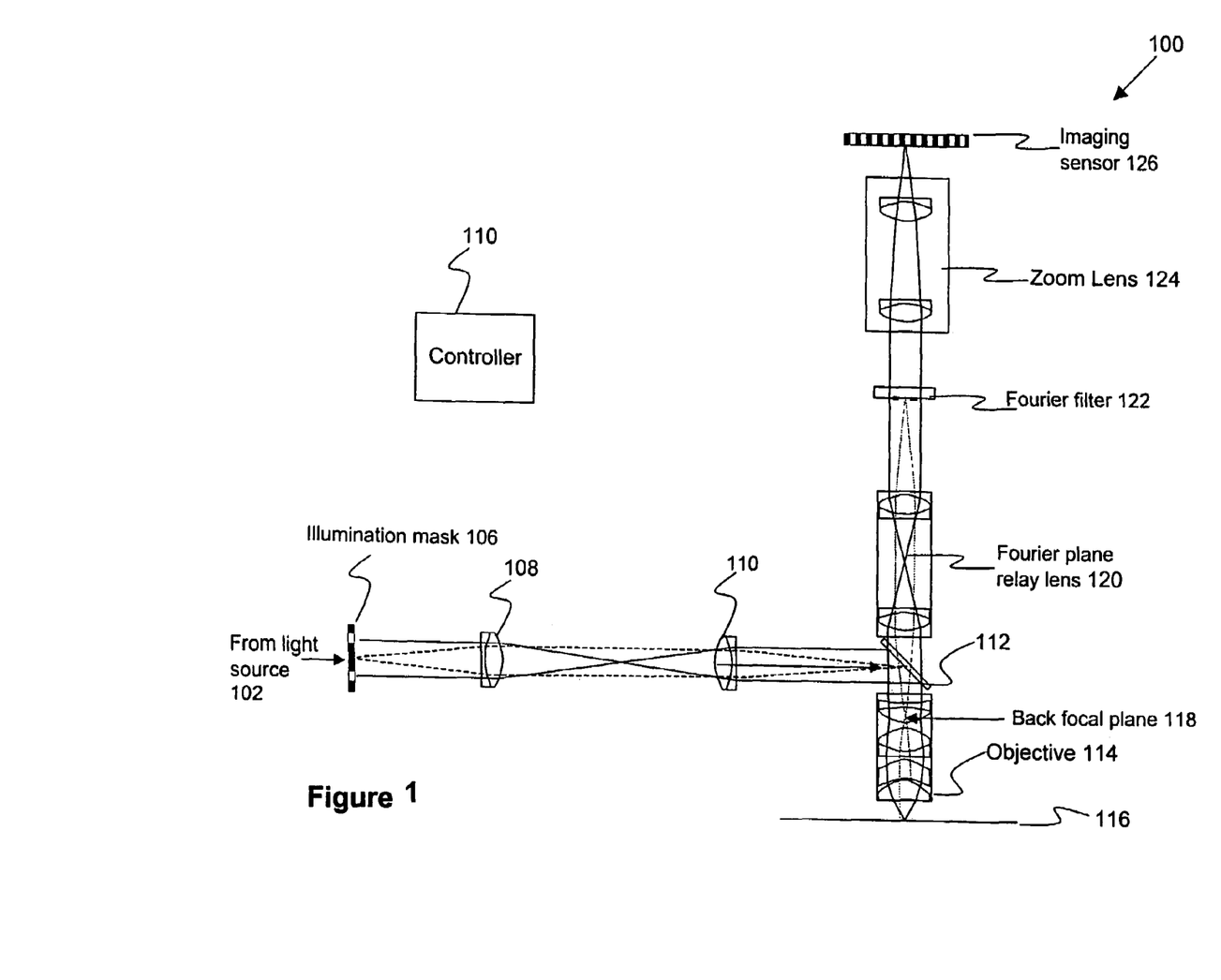
FIG. 1 is a diagrammatic representation of an inspection system having a complex Fourier filter in accordance with one embodiment of the present invention.

FIG. 1 is a diagrammatic representation of an inspection system 100 having a complex Fourier filter in accordance with one embodiment of the present invention. As shown, the inspection system 100 includes a light source 102 for generating an incident beam having a relatively narrow bandwidth so as to produce meaningful phase differences in the resulting output beam to which the complex Fourier filter may be applied for contrast enhancement effects. However, this bandwidth need not be overly narrow. For example, variations in the light emission wavelength of +/−50 nm may be acceptable.

In an alternative embodiment, the illumination source may be in the form of multiple illuminations sources which are selectively directed onto a plurality of optical fibers. These fibers then are arranged to output a plurality of incident beams with a spatial profile that is dependent on the selected illumination sources. The fibers may also be coupled with a fiber modulator which operates to substantially eliminate the speckle noise which may be present in the incident beams to thereby produce a more uniform, incoherent illumination. For example, the fiber modulator may be a piezoelectric modulator which operates to stretch the fibers so as to change the phase difference between the modes inside the multi-mode fibers to therefore reduce the spatial coherence to produce a speckle free illumination. Several embodiments of such an arrangement are further described in U.S. Provisional Application No. 60/533,741, entitled ILLUMINATION APPARATUS AND METHODS, filed 29 Dec. 2003, by Mehdi Vaez-Iravani and Guoheng Zhao, which application is incorporated herein by reference in its entirety.

Referring back to FIG. 1, the incident beam then passes through a number of lenses which serve to relay the beam towards a sample 116. In the illustrated embodiment, the incident beam passes through lens 108 which collimates the incident beam and then through lens 110 which converges the incident beam. The incident beam is then received by beam splitter 112 which then reflects the incident beam through objective lens 114 which focuses the incident beam onto sample 116 at one or more incident angles.

After the incident beam impinges on the sample, the light is then reflected (and/or transmitted) and scattered from the sample 116, which is referred to herein as an "output beam." The inspection system also includes any suitable lens arrangements for directing the output light towards a detector. In the illustrated embodiment, the output beam passes through beam splitter 112, Fourier plane relay lens 120, complex Fourier filter 122, and zoom lens 124. Since the back focal plane of the objective lens is typically not accessible, the Fourier plane relay lens generally relays the back focal plane or Fourier plane of the sample to form a relayed conjugate plane at which position complex Fourier filter 122 is positioned, whose purpose is further described below. In future lens arrangements, the back focal plane may be more accessible so that a Fourier plane relay lens 120 is not required.

In general, the back focal plane or its relayed conjugate plane represents the Fourier transform of the near field image of the sample. These planes are referred herein as Fourier planes. Since each point at the Fourier plane represents one plane wave, a complex Fourier filter (or in some embodiments, mask) placed at the Fourier plane can be arranged to selectively alter the amplitude or phase of each plane wave to enhance the contrast for certain structures that would normally result in poor contrast under conventional imaging modes. The system 100 may also include an illumination aperture 106, which is also needed so that specular and scattered light (diffraction orders) of the output beam can be defined spatially at the Fourier plane. Alternatively, the fibers and multiple light sources described above may be utilized as an illumination aperture). Otherwise, the specular and scattered light would be integrated and spatially indistinguishable from each other.

After going through the Fourier filter 122, the output beam may then pass through zoom lens 124 which serves to magnify the image of the sample 116. The output beam then impinges upon detector 126. By way of example, the detector may be in the form of a CCD (charge coupled device) or TDI (time delay integration) detector.

The inspection system also includes a controller 110 in the form of any suitable combination of software and hardware (e.g., such as one or more memory and processors programmed to operate the system components and analyze data from such components). The controller 110 is generally configured to control various components of the inspection system 100. For instance, the controller may control activation of the illumination source 102, etc. The controller 110 may also receive the image or signal generated by the detector 126 and be configured to analyze the resulting image or signal to determine whether defects are present on the sample, characterize defects present on the sample, or otherwise characterize the sample. For instance, an image of the sample may be compared to a reference image that is obtained from another die, an adjacent area, or a design database. This comparison may result in a discrepancy between the two images which is characterized as a defect when the difference is significant (e.g., exceeds a predetermined threshold).

The complex Fourier filter 122 may be formed from any suitable material for enhancing the contrast between particular spatial portions of the output beam (e.g., specular versus scattered spatial portions). In one implementation, the phase and amplitude of the specular light portions are altered so as to distinguish them from the phase and amplitude of the scattered light portions. The phase difference and amplitude difference between various spatial portions are generally dependent on the thickness and composition of the Fourier filter material at the various corresponding spatial portions of the Fourier filter. In one embodiment, Fourier filter areas which correspond to scattered light portions of the output beam will have a different thickness and film material than Fourier filter areas which correspond to specular light portions of the output beam. The particular arrangement of the complex Fourier filter also depends on the particular arrangement of the illumination aperture 106 whose arrangement affects the spatial position of the scattered versus the specular light. The illumination aperture 106 configuration is selected according to the requirements of the particular application.

Figure 2A:
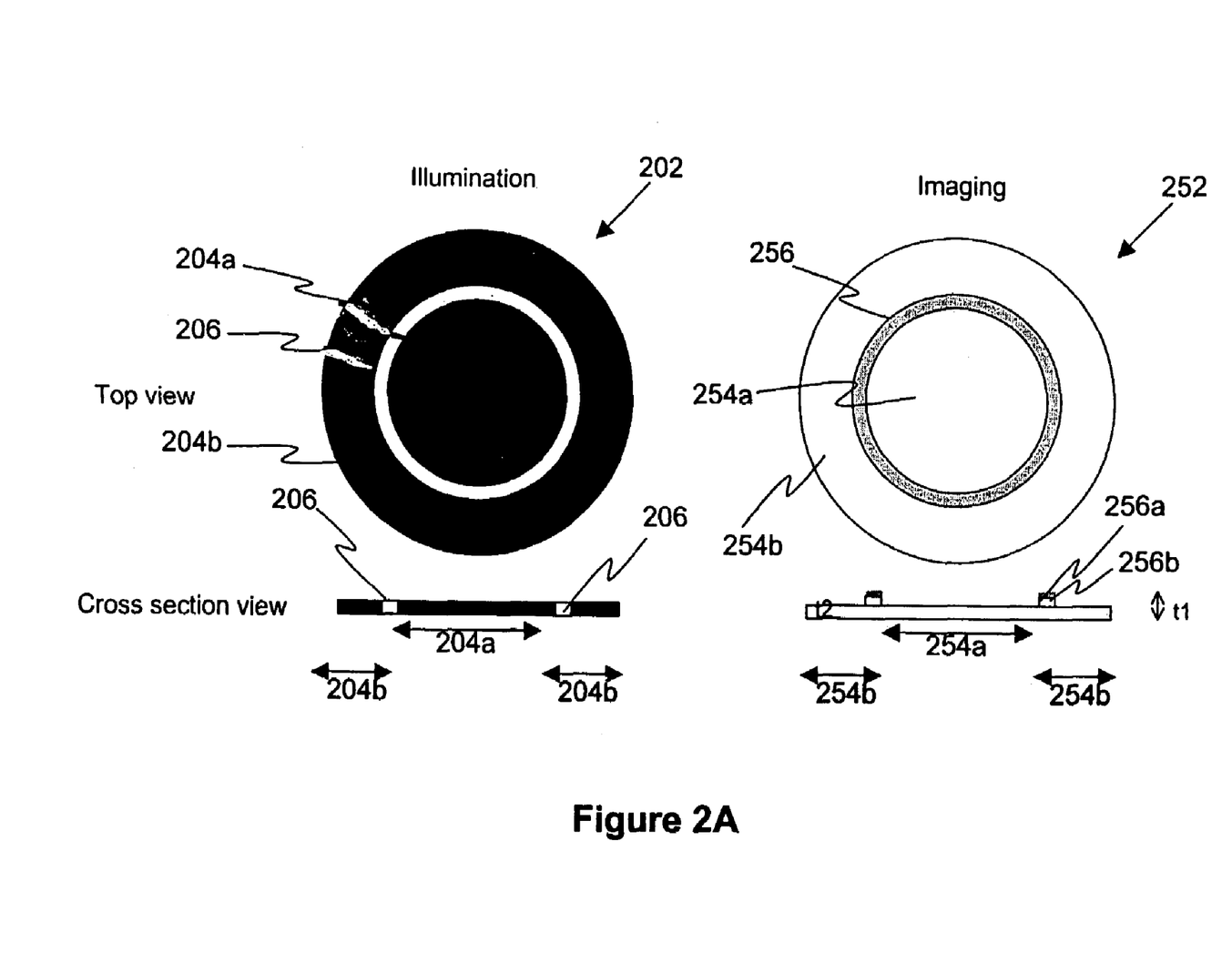
FIG. 2A is a diagrammatic representation of an illumination aperture and a Fourier filter in accordance with a specific implementation of the present invention.

FIG. 2A is a diagrammatic representation of an illumination aperture 202 and a complex Fourier filter 252 in accordance with a specific application of the present invention. In this implementation, the illumination aperture 202 has an overall circular shape as shown in a top view although other suitable shapes may be used. Also shown in the top view, the illumination aperture 202 has an opaque circular center portion 204a and an opaque outer ring 204b. An inner ring portion 206 positioned between the opaque circular center 204a and the opaque outer ring 204b is left transparent. The transparent inner ring 206 and opaque portions 204 of the illumination aperture 202 are also shown in a cross section view. This configuration is typically seen in a dark field inspection mode. This illumination aperture 202 allows zero order angles of the incident beam to be better defined since zero order light is more readily definable by smaller apertures, such as the thin inner ring 206. However, light efficiency is preferably balanced against optimization of specular definition.

The imaging aperture or complex Fourier filter 252 is also shown in a top view and a cross section view. As shown in the top view, the imaging aperture 252 includes a transparent inner circular portion 254a and a transparent outer ring portion 254b. An inner ring portion 256 contains a thin film that is selected to cause a phase difference and amplitude difference between the spatial portions of the output beam which pass through the inner ring portion 256 and the remaining portions of the output beam which pass through the transparent portions 254. In this example, the thin film 256 corresponds with the specular light, while the transparent portions 254 correspond with the non-specular light portions of the output beam. The thin film portion 256 of the imaging aperture 252 corresponds to the transparent section 206 of the illumination aperture 202, while the transparent sections 254 of the imaging aperture 252 correspond to the opaque portions 204 of the illumination aperture 202.

Alternatively, the thin film section may be switched with the transparent section of the imaging aperture. In this application, any suitable arrangement may be used which enhances phase contrast and amplitude contrast between the specular and scattered light portions (or zero versus higher orders) of the output beam.

As shown in the cross section view, the transparent portions of the imaging aperture 252 may be formed from a transparent substance, such as glass or fused silica substrate. The inner ring portion may also include this transparent substance which is covered with a thin film 256a, such as a dielectric film. In the illustrated embodiment, the inner ring portion 256 has a thickness t1 that varies from the transparent portions 254 thickness t2. In this example, the inner ring portion 256 thickness t1 is due to steps 256b in the transparent substance which underlies the thin film portion 256a. The steps may be formed in any suitable manner such as etching the transparent substrate. The thin film may also be formed by any suitable technique, such as a deposition or an implantation procedure.

The composition of the thin film, the relative thickness of the different portions of the Fourier filter, and the step heights may be selected so that contrast is enhanced between the specular and the scattered portions of the output beam. These configurations may be determined based on a simulation of different configurations and their resulting output beam profiles when there is a defect present on the sample. The configuration which produces the largest contrast may then be selected. Alternatively, the Fourier filter configuration may be based on experimental results on different Fourier filter configurations for particular defect types. The thin film may be any suitable material which produces an optimized phase contrast and amplitude contrast, such as a dielectric coating, etc.

After the Fourier filter configuration is selected, the Fourier filter then serves to alter the interference between different spatial portions of the output beam, e.g., the specular and the scattered light portions. In effect, the Fourier filter alters the phase relation between some of the spatial frequencies in the sample with respect to other spatial frequencies in the sample. When scattered light is the result of a small defect, the scattered light from such defect is enhanced relative to the specular light from defect-free portions of the sample. In other words, this Fourier filter embodiment results in enhanced contrast.

Figure 2B:
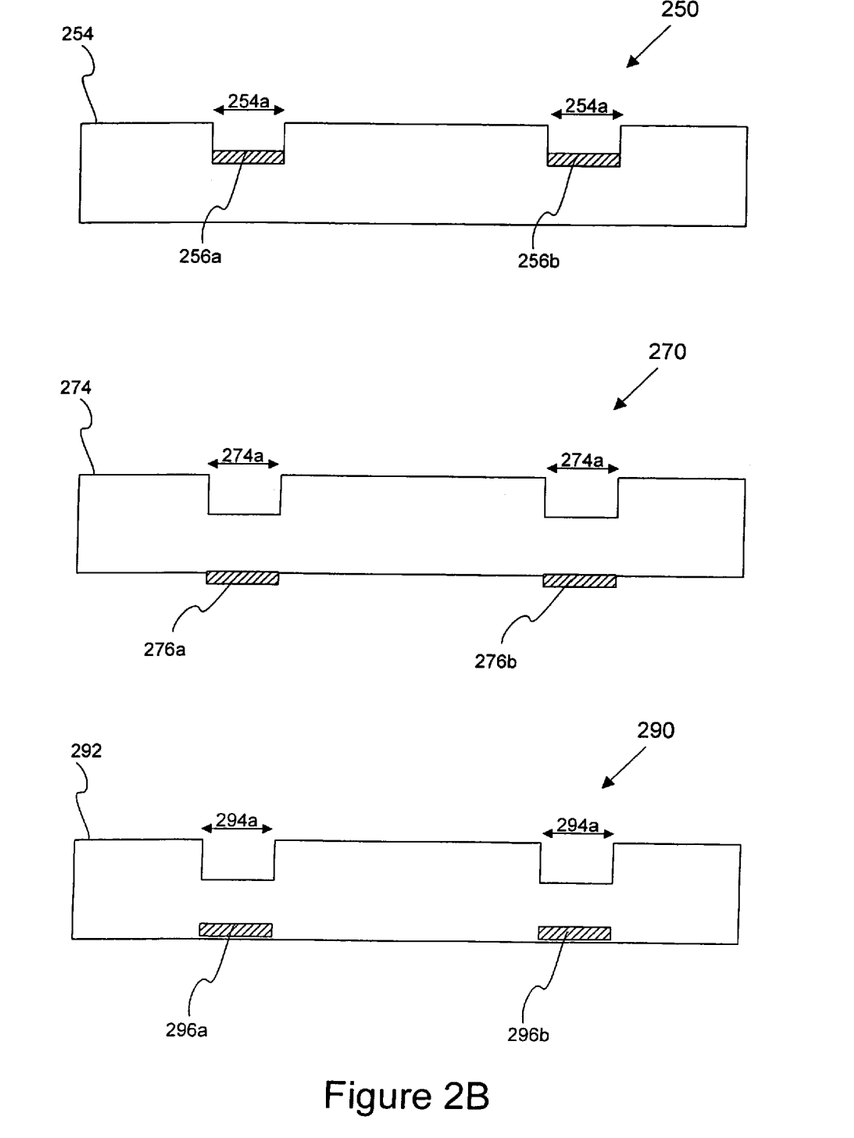
FIG. 2B are side view diagrammatic representations of a plurality of alternative Fourier filters in accordance with a specific implementation of the present invention.

FIG. 2B is a diagrammatic representation of a plurality of alternative Fourier filters in accordance with a specific implementation of the present invention. The complex Fourier filter may include trenches, instead of steps. As shown, complex Fourier filters 250, 270, and 290 include trenches 254, 274, 294, respectively. The thin film may also be placed anywhere with respect to the trenches. The complex Fourier filter 250 includes thin film portions 256a and 256b which are positioned within the trenches 254a and 254b, respectively. In the complex Fourier filter 270, the thin film portions 276a and 276b are alternatively placed on a side which is opposite the side of the corresponding trenches 274a and 274b, respectively. In both complex Fourier filter embodiments 250 and 270, the thin film portions are comprised of material which is deposited on the transparent substrated, 254 or 274. In another complex Fourier filter implementation 290, the thin film portions 296a and 296b are implanted into the substrate 292 at positions underneath the trenches 294a and 294b, respectively.

In any of the above described complex Fourier filter implementations, the thin film portions and their corresponding steps or trenches may be placed so as to filter the scattered light spatial portions, as opposed to the specular light portions. However, it may be easier to manufacture a complex Fourier filter having thin film portions in a relatively smaller area of the total Fourier filter area, as opposed to taking a relatively large area with a scattered thin film area.

Figure 3:
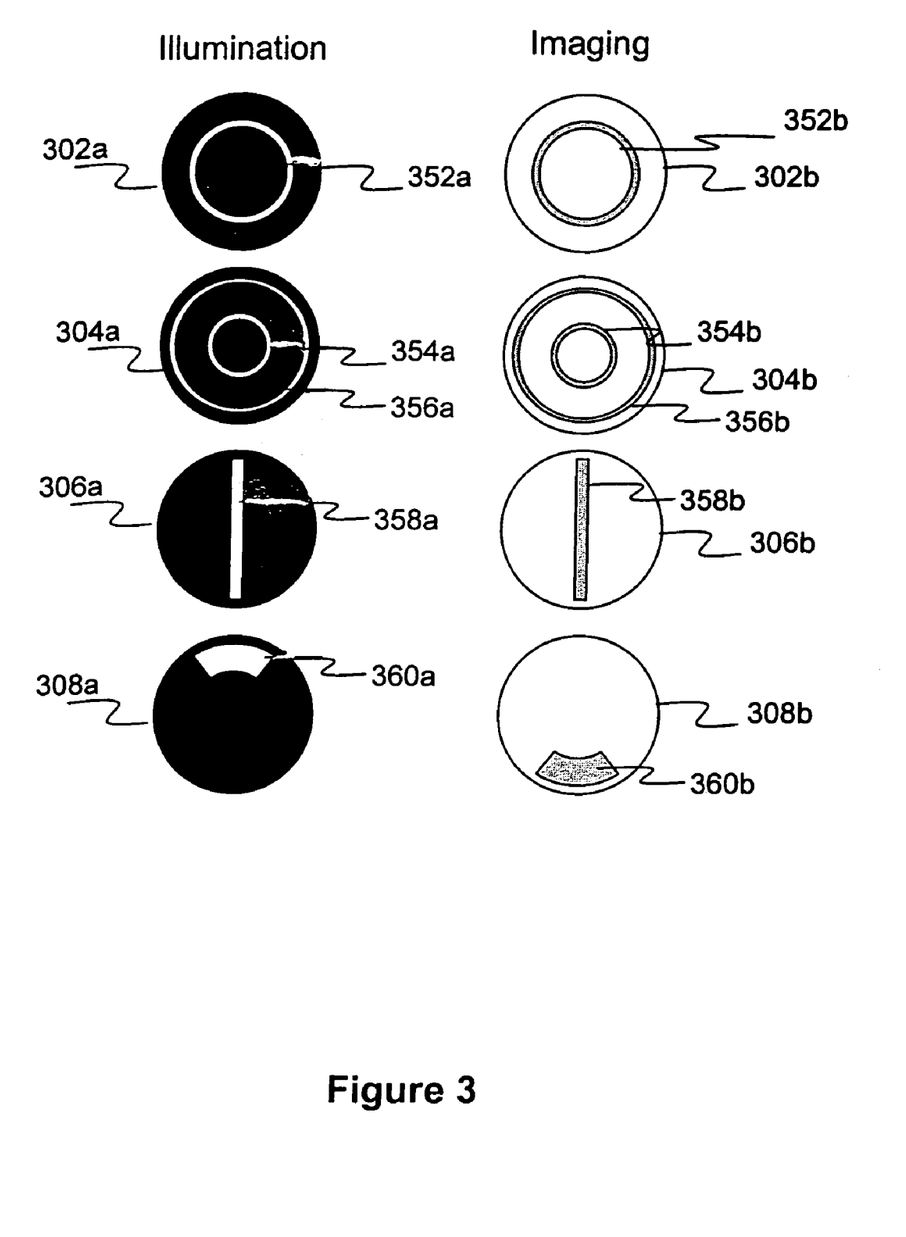
FIG. 3 are top view diagrammatic representations of various illumination apertures and corresponding Fourier filters in accordance with alternative implementations of the present invention.

In other inspection applications, any suitable arrangement of illumination aperture and contrasting Fourier filter (or imaging aperture) may be utilized. FIG. 3 is a diagrammatic representation of various illumination apertures and corresponding Fourier filters in accordance with alternative implementations of the present invention. Illumination aperture 302a and imaging aperture 302b are similar to the examples shown in FIG. 2A.

Illumination aperture 304a includes two transparent rings formed concentrically with opaque circular sections. The complimentary imaging aperture 304b includes thin film rings that correspond to the transparent rings of the illumination aperture 304a. The transparent sections of the imaging aperture 304b also correspond to the opaque sections of illumination aperture 304a. This arrangement has several advantages. For example, a double ring illumination aperture is more light efficient than a single ring aperture.

In another arrangement, illumination aperture 306a contains a single slit of transparency surrounded by opaque regions. The complimentary imaging aperture 306b contains a single slit of a thin film portion surrounded by transparent portions. This configuration may be useful for those applications in which the sample represents a two-dimensional array format, and one is interested in eliminating the various components. Under those circumstances, it is quite simple to construct an appropriate filter which will consist of a series of parallel opaque stripes, whose location corresponds to the various orders.

Illumination aperture 308a includes a transparent arc portion 309 surrounded by opaque areas. Thus, the complimentary imaging aperture 308b contains a complimentary thin film arc portion 358. In this embodiment, the illumination and imaging apertures are asymmetric and may be used with asymmetric structures on the sample. Asymmetric structures tend to scatter in a particular direction.

Figure 4A:
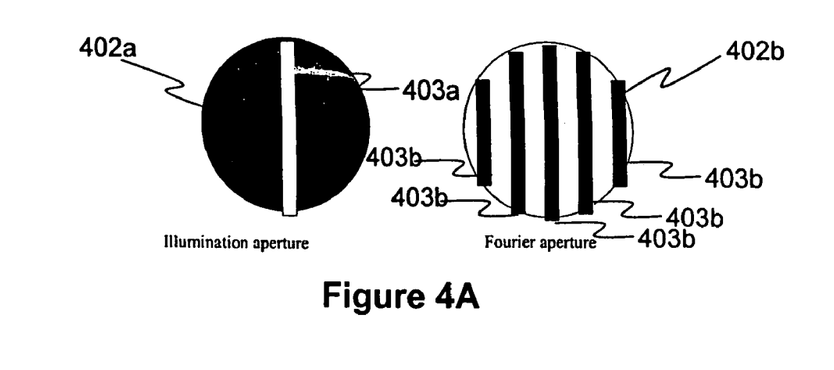
FIG. 4A is a diagrammatic representation of a Fourier illumination aperture and a corresponding Fourier filter for filtering periodic structures from the output beam in accordance with one embodiment of the present invention.

In yet another application, a complex Fourier filter of the present invention may be used to filter out repetitive patterns on the output beam due to repeating device structures in the sample. FIG. 4A is a diagrammatic representation of a Fourier illumination aperture and a corresponding Fourier filter for filtering periodic structures from the output beam. In this implementation, the illumination aperture contains a thin slit transparent portion 403a. The complimentary Fourier aperture 402b includes thin film slit portions 403b to filter out the repetitive structures of the output beam (e.g., higher orders from the scattered repeating structures). In this case, the slit portions 403b of complex Fourier filter 402b are completely opaque so as to block the zero and higher order spatial portions from the repeating structures on the sample.

Figure 4B:
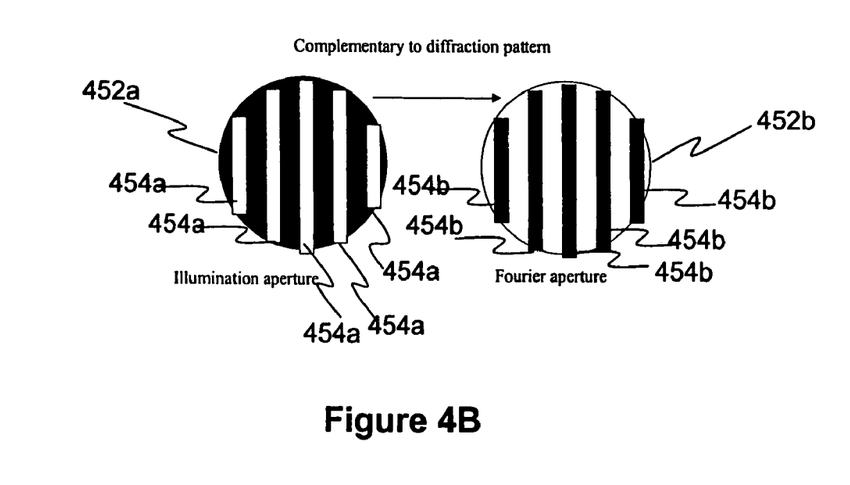
FIG. 4B is a diagrammatic representation of a periodic illumination aperture and a corresponding Fourier filter for improving light efficiency while filtering period structures from the output beam in accordance with one embodiment of the present invention.

FIG. 4B is a diagrammatic representation of a periodic illumination aperture and a corresponding Fourier filter for improving light efficiency while filtering period structures from the output beam in accordance with one embodiment of the present invention. In this implementation, the illumination aperture is a compliment of the Fourier aperture of FIG. 4A. As shown, the illumination aperture 452a includes a plurality of thin slit transparent portions 454a that compliment thin film slit portions 454b of Fourier aperture 452b. Similar to the previous case, the slit portions 454b of complex Fourier filter 452b are completely opaque so as to block the zero and higher order spatial portions from the repeating structures on the sample.

Figure 5:
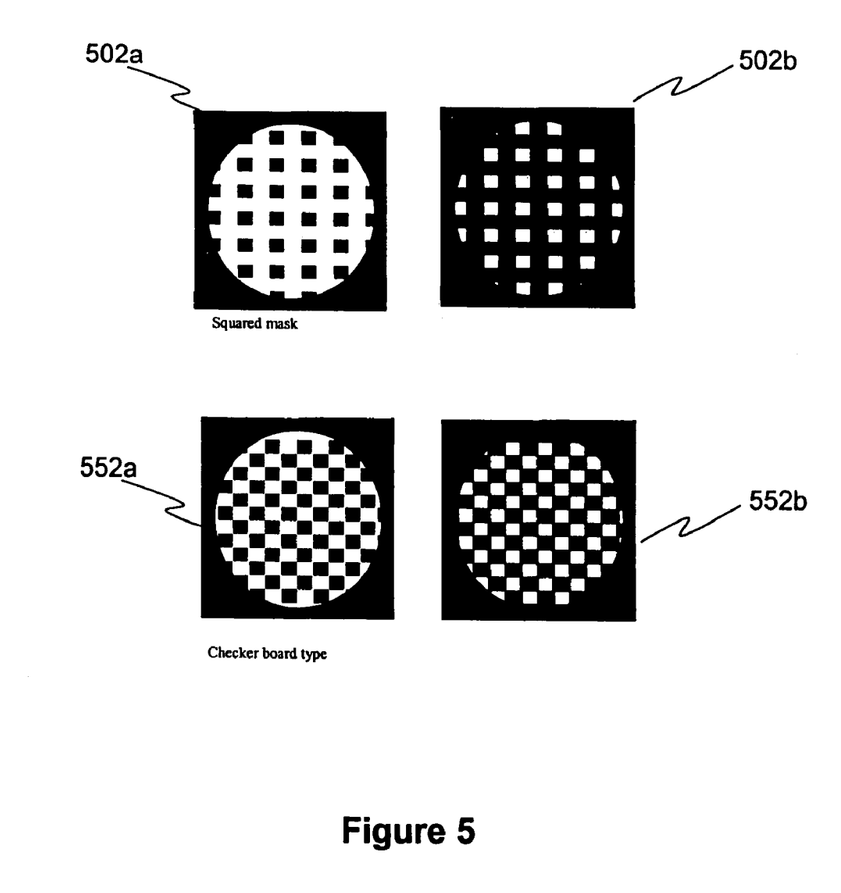
FIG. 5 are top view diagrammatic representations of two-dimensional periodic Fourier filter masks in accordance with two embodiments of the present invention.

FIG. 5 is a diagrammatic representation of two-dimensional periodic Fourier filter masks in accordance with two embodiments of the present invention. As shown, the illumination aperture 502a includes an array of opaque squares, while the Fourier aperture 502b includes an array of transparent portions surrounded by thin film areas. In another implementation, an illumination aperture 552a includes a checkerboard pattern of opaque squares, while its complimentary Fourier filter 552 includes a checkerboard pattern of transparent squares surrounded by thin film squares. These implementations allow increased light efficiency during inspection of array type structures, such as memory arrays.

Figure 6:
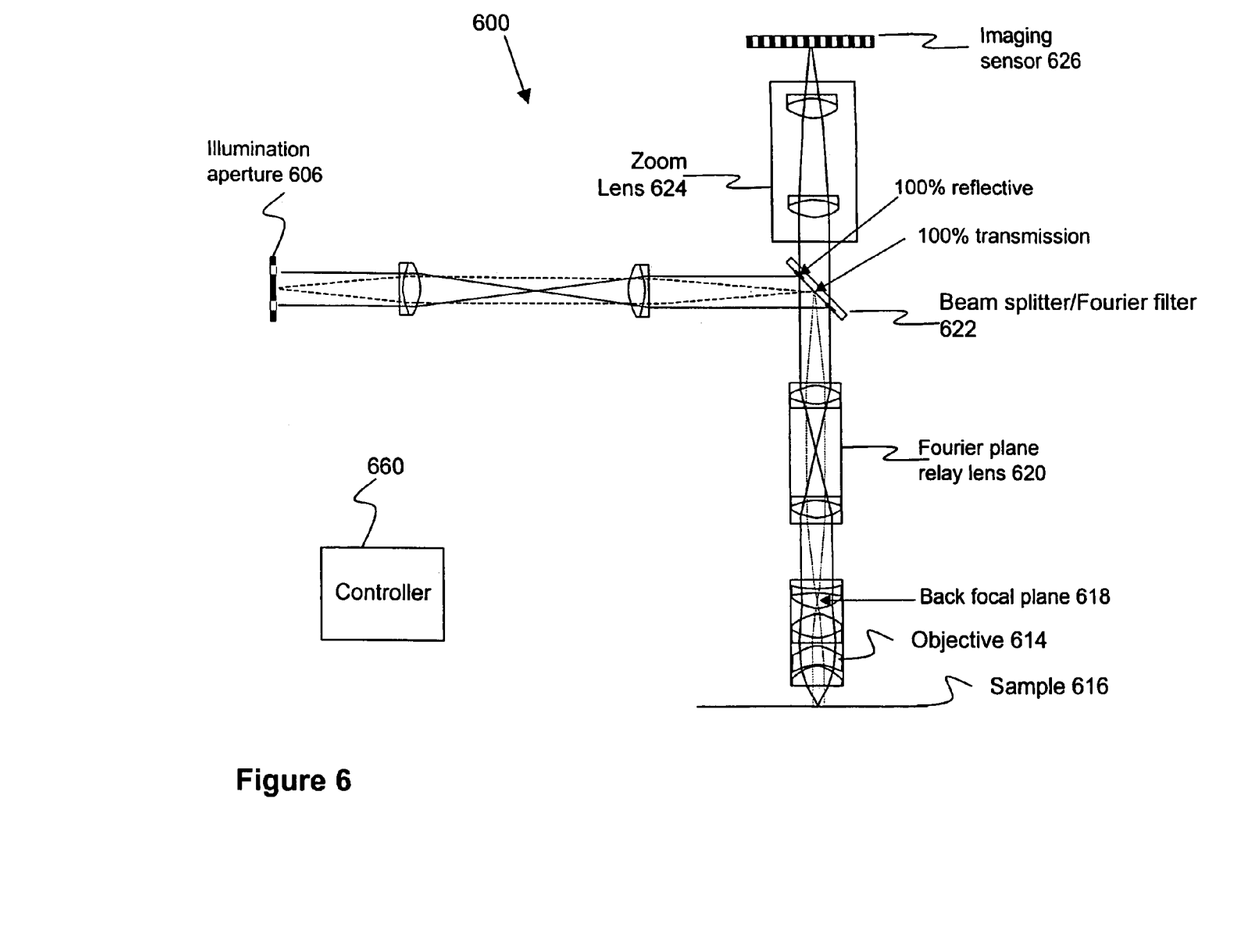
FIG. 6 is a diagrammatic representation of an inspection system having a complex Fourier filter that is combined with a beam splitter in accordance with an alternative embodiment of the present invention.

FIG. 6 is a diagrammatic representation of an inspection system having a complex Fourier filter that is combined with a beam splitter in accordance with an alternative embodiment of the present invention. The system 600 of FIG. 6 is similar to the system of FIG. 1, except that the Fourier filter is integrated into a beam splitter 622. In this embodiment, specific portions of the incident beam are reflected from reflective portions of the beam splitter 622 and the reflected portions then pass through the Fourier plane relay lens 620 and objective 614 onto sample 616. The combination beam splitter/ Fourier filter 622 may be switchably removed and replaced with a conventional 50/50 beam splitter, e.g., during a bright field inspection.

The output beam then passes through the beam splitter, which now acts as a Fourier filter 622 and zoom lens 624 towards an imaging sensor 626. The Fourier filter 622 includes portions that are close to 100% reflective and portions that are close to 100% transmissive. The reflective portions were used to direct specific spatial portions of the incident light towards the sample, while the transmissive portions transmit specific spatial portions of the output beam towards sensor 626. Since the reflective and transmissive portions of the complex Fourier filter are arranged together on the beam splitter, the transmissive portions inherently complement the reflective portions of the beam splitter/ Fourier filter 622. The reflective and transmissive portions may be arranged with respect to one another in any suitable manner, such as combining any of the illumination and imaging apertures described above.

Figure 7:
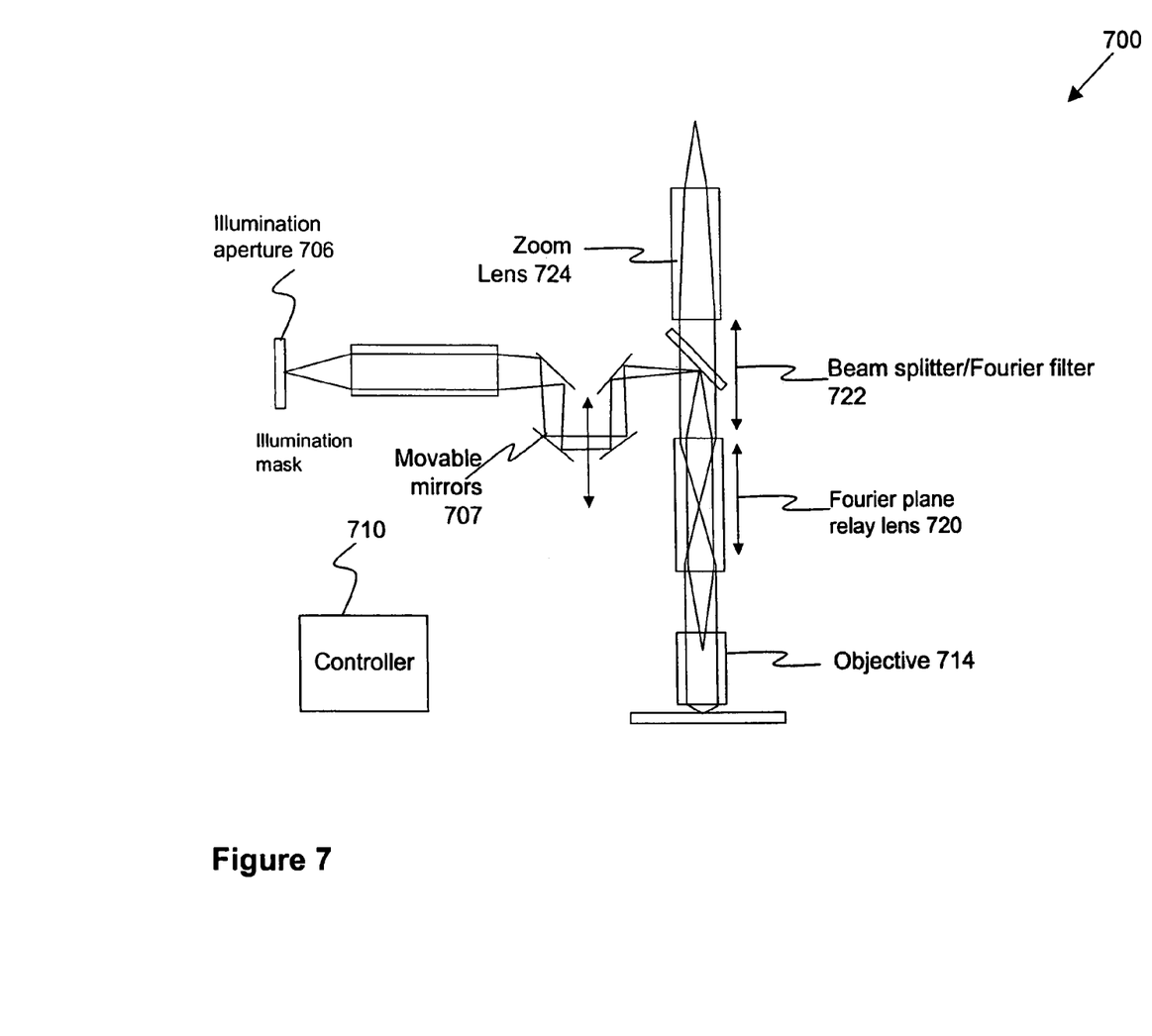
FIG. 7 is a diagrammatic representation of an inspection system having a complex Fourier filter that is combined with a beam splitter and is optically adjustable in accordance with another embodiment of the present invention.

The illumination and complex Fourier filter (or beam splitter type Fourier filter) arrangement depends on the particular requirements of the application. Preferably, the arrangement is adjustable so that the same system may be adjusted to have different illumination and complex Fourier filter (or beam splitter/Fourier filter) configurations. FIG. 7 is a diagrammatic representation of an inspection system having a complex Fourier filter that is combined with a beam splitter and is optically adjustable in accordance with another embodiment of the present invention. This system includes components similar to the components in the system 600 of FIG. 6. However, this system 600 includes a movement mechanism for moving the Fourier relay lens 720 and beam splitter/Fourier filter 722 which movement results in an optical adjustment of the Fourier filter dimension. Additionally, a group of movable mirrors in the illumination mirrors 707 are movable such that when the beam splitter/ Fourier filter 722 is moved, the conjugate image of the illumination mask remains constant. Although this embodiment is described as implementing the beam splitter type filter which either blocks or transmits output beam portions, of course, it may also be utilized with the separate complex Fourier filter that has thin film and transparent portions, e.g., as the filter of system 100 of FIG. 1.

Although the foregoing invention has been described in some detail for purposes of clarity of understanding, it will be apparent that certain changes and modifications may be practiced within the scope of the appended claims. For example, although the Fourier filters are described herein as being implemented in reflection type inspection systems, they may be easily applied to transmission or combinational reflection and transmission type systems. Additionally, the Fourier filters of the present invention may be implemented within any suitable microscopy system. Therefore, the described embodiments should be taken as illustrative and not restrictive, and the invention should not be limited to the details given herein but should be defined by the following claims and their full scope of equivalents.

What is claimed is:

1. An apparatus for inspecting or imaging a semiconductor sample, comprising:

an illumination lens arrangement for directing an incident beam towards a sample;

an illumination aperture that include at least a first area and a second area, the first area being arranged to block a blocked spatial portion of the incident beam and the second area being arranged to transmit a transmitted spatial portion of the incident beam towards the sample;

an output lens arrangement for directing an output beam from the sample towards a detector, the output beam comprising a specular portion and a scattered light portion; and a complex Fourier filter positioned within a Fourier plane of the sample, wherein the complex Fourier filter has at least a first area and a second area that vary in material composition and/or thickness, wherein the relative material compositions and thickness of the first and second area are selected so as to alter a phase of the specular portions of the output beam relative to the scattered portions of the output beam so as to enhance contrast between the scattered and specular light portions of the output beam.

2. An apparatus as recited in claim 1, wherein the first area of the complex Fourier filter corresponds to the first area of the illumination aperture and the second area of the complex Fourier filter corresponds to the second area of the illumination aperture.

3. An apparatus as recited in claim 2, wherein the first area of the complex Fourier filter corresponds to scattered portions of the output beam and the second area of the complex Fourier filter corresponds to specular portions of the output beam.

4. An apparatus as recited in claim 2, wherein the first area of the complex Fourier filter corresponds to specular portions of the output beam and the second area of the complex Fourier filter corresponds to scattered portions of the output beam.

5. An apparatus as recited in claim 2, wherein the first area of the complex Fourier filter is formed from a transparent substrate having a first thickness and the second area of the complex Fourier filter is formed from a thin film and the transparent substrate, the second area having a second thickness which differs from the first thickness.

6. An apparatus as recited in claim 5, wherein the first area of the complex Fourier filter corresponds to scattered portions of the output beam and the second area of the complex Fourier filter corresponds to specular portions of the output beam.

7. An apparatus as recited in claim 6, wherein the first area of the complex Fourier filter is formed from a step in the transparent substrate.

8. An apparatus as recited in claim 7, wherein the step height is also selected so as to alter a phase of the specular portions of the output beam relative to the scattered portions of the output beam so as to enhance contrast between the scattered and specular light portions of the output beam.

9. An apparatus as recited in claim 5, wherein the first area of the complex Fourier filter is formed from a trench in the transparent substrate.

10. An apparatus as recited in claim 9, wherein the thin film is positioned within the trench of the first area.

11. An apparatus as recited in claim 9, wherein the thin film is positioned underneath the trench of the first area, implanted within the transparent substrate.

12. An apparatus as recited in claim 9, wherein the thin film is positioned on a surface of the transparent substrate that is opposite a surface of the transparent substrate that forms the trench of the first area.

13. An apparatus as recited in claim 5, wherein the thin film is a dielectric material having a thickness and a composition which allows a corresponding portion of the output beam to pass there through with an altered phase and amplitude.

14. An apparatus as recited in claim 5, wherein the thin film is implanted in a portion of the transparent substrate.

15. An apparatus as recited in claim 5, wherein the thin film is deposited on a portion of the transparent substrate.

16. An apparatus as recited in claim 5, wherein the transparent substrate is formed from a glass or a fused silica material.

17. An apparatus as recited in claim 2, wherein the first area of the illumination aperture includes an inner opaque circular portion that blocks an inner circular portion of the incident beam, the second area of the illumination aperture being a transparent ring that surrounds the inner opaque circular portion and transmits a ring portion of the incident beam, the first area of the complex Fourier filter includes an inner transparent circular portion that transmits an inner circular portion of the output beam; and the second area of the complex Fourier filter includes a thin film ring that surrounds the inner transparent portion of the complex Fourier filter and changes a phase of a ring portion of the output beam, wherein the complex Fourier filter is positioned so that the some of the scattered light portions of the output beam pass through the inner transparent circular portion and the specular light portions are filtered through the thin film ring of the complex Fourier filter.

18. An apparatus as recited in claim 17, wherein the first area of the illumination aperture further includes an outer opaque ring that surrounds the transparent ring and blocks an outer ring portion of the incident beam, and the first area of the complex Fourier filter further including an outer transparent ring that surrounds the thin film ring of the complex Fourier filter and transmits an outer ring portion of the incident beam, wherein the complex Fourier filter is positioned so that some of the scattered light portions of the output beam pass through the outer transparent ring of the complex Fourier filter.

19. An apparatus as recited in claim 18, wherein the thin film ring of the complex Fourier filter has a different thickness than the other portions of the inner transparent portion and the outer transparent portion of the complex Fourier filter.

20. An apparatus as recited in claim 19, wherein the second area of the illumination aperture further includes a second transparent ring adjacent to the outer opaque ring and the first area of the illumination aperture further includes a second outer opaque ring adjacent to the second transparent ring, and wherein the second area of the complex Fourier filter further includes a second thin film ring that has the same thickness as the first thin film, the second thin film being adjacent to the outer transparent ring and the first area of the complex Fourier filter further including a second transparent ring adjacent to the second thin film ring.

21. An apparatus as recited in claim 2, wherein the second area of the illumination aperture includes a slit shaped opaque portion that blocks a slit shaped portion of the incident beam, the first area of the illumination aperture being a transparent portion that surrounds the slit shaped opaque portion of the illumination aperture and transmits a corresponding portion of the incident beam, the second area of the complex Fourier filter includes thin film slit shaped portion that transmits a slit shaped portion of the output beam and changes a phase of a slit shaped portion of the output beam; and the first area of the complex Fourier filter includes a transparent portion that surrounds the thin film slit portion and transmits a corresponding portion of the output beam, wherein the complex Fourier filter is positioned so that some of the scattered light portions of the output beam pass through the transparent portion and the specular light portions are filtered through the thin film slit portion of the complex Fourier filter.

22. An apparatus as recited in claim 2, wherein the second area of the illumination aperture includes an arc shaped opaque portion that blocks an arc shaped portion of the incident beam, the first area of the illumination aperture includes a transparent portion that surrounds the arc shaped opaque portion of the illumination aperture and transmits a corresponding portion of the incident beam, the second area of the complex Fourier filter includes a thin film arc shaped portion that transmits an arc shaped of the output beam and changes a phase of the arc shaped of the output beam; and the first area of the complex Fourier filter includes a transparent portion that surrounds the arc shaped portion and transmits a corresponding portion of the output beam, wherein the complex Fourier filter is positioned so that the some of the scattered light portions of the output beam pass through the transparent portion and the specular light portions are filtered through the arc shaped portion of the complex Fourier filter.

23. An apparatus as recited in claim 1, wherein the output beam is transmitted through the sample.

24. An apparatus as recited in claim 1, wherein the output beam is both reflected from and transmitted through the sample.

25. An apparatus as recited in claim 1, wherein the output beam is both reflected and scattered from the sample.

26. An apparatus as recited in claim 1, wherein the illumination aperture is in the form of a plurality of illumination sources which are configurable to be selectively directed onto a first plurality of ends of a plurality optical fibers that are arranged to output the incident beam in the form of a plurality of incident beams from a second plurality of ends of the fibers, wherein the fibers are coupled with a fiber modulator which is operable to substantially eliminate the speckle noise of the incident beams.

27. An apparatus as recited in claim 1, wherein the illumination lens arrangement and the output lens arrangement are both movable so as to adjust the complex Fourier filter dimensions.

28. An apparatus as recited in claim 1, wherein the relative material compositions and thickness of the first and second area are further selected so as to alter an amplitude of the specular portions of the output beam relative to the scattered portions of the output beam so as to enhance contrast between the scattered and specular light portions of the output beam.

29. A method for inspecting a semiconductor sample having repeating structures, comprising:

directing an incident beam towards a sample along a path having an illumination mask that include at least a plurality of first areas surrounded by at least a second area, the first areas being arranged to transmit a plurality of blocked illumination spatial portion of the incident beam and the second area being arranged to block a transmitted spatial portion of the incident beam towards the sample;

directing an output beam from the sample towards a detector, the output beam comprising a specular portion and a scattered light portion, wherein the output beam is directed to the detector along a path having a complex Fourier mask positioned within a Fourier plane of the sample, wherein the complex Fourier mask has at least a plurality of first areas that are transparent and a second area that surrounds the first areas and is opaque, wherein the first and second area positions are selected so as to filter portions of the output beam corresponding to repeating structures on the sample, wherein the first areas of the complex Fourier filter correspond to the first areas of the illumination aperture and the second area of the complex Fourier filter corresponds to the second area of the illumination aperture.

30. An apparatus for inspecting a semiconductor sample having repeating structures, comprising:

an illumination lens arrangement for directing an incident beam towards a sample;

an illumination mask that include at least a plurality of first areas surrounded by at least a second area, the first areas being arranged to transmit a plurality of blocked illumination spatial portion of the incident beam and the second area being arranged to block a transmitted spatial portion of the incident beam towards the sample;

an output lens arrangement for directing an output beam from the sample towards a detector, the output beam comprising a specular portion and a scattered light portion; and a complex Fourier mask positioned within a Fourier plane of the sample, wherein the complex Fourier mask has at least a plurality of first areas that are transparent and a second area that surrounds the first areas and is opaque, wherein the first and second area positions are selected so as to filter portions of the output beam corresponding to repeating structures on the sample, wherein the first areas of the complex Fourier filter correspond to the first areas of the illumination aperture and the second area of the complex Fourier filter corresponds to the second area of the illumination aperture.

31. An apparatus as recited in claim 30, wherein the illumination mask and the complex Fourier filter are integrated into a beam splitter that forms part of both the illumination lens arrangement and the output lens arrangement, wherein the beam splitter has a reflective portion and a transmissive portion, wherein the reflective portion corresponds to the first areas of the illumination mask and the first areas of the complex Fourier filter and the transmissive portion corresponds to the second area of the illumination mask and the second area of the complex Fourier filter.

32. An apparatus as recited in claim 31, wherein at least a portion of the output lens arrangement and the complex Fourier filter are movable so as to allow adjustment of the complex Fourier filter's dimensions.

33. An apparatus as recited in claim 32, wherein the illumination lens arrangement includes a group of movable mirrors so as to keep a conjugate image of the illumination mask constant during movement of the at least a portion of the output lens arrangement and the complex Fourier filter.

34. An apparatus as recited in claim 30, wherein the first areas of the illumination aperture are a plurality of slits, and the first areas of the complex Fourier filter are a plurality of opaque slit portions.

35. An apparatus as recited in claim 30, wherein the first areas of the illumination aperture are an array of transparent portions and the second area of the illumination aperture is an opaque portion, and wherein the first areas of the complex Fourier filter are an array of opaque portions and the second area of the complex Fourier filter is a transparent portion.

36. An apparatus as recited in claim 30, wherein the first areas of the illumination aperture are a checkerboards pattern of transparent portions and the second area of the illumination aperture is an opaque portion, and wherein the first areas of the complex Fourier filter are a checkerboards pattern of opaque portions and the second area of the complex Fourier filter is a transparent portion.

37. A method for inspecting or imaging a semiconductor sample, comprising:
  directing an incident beam towards a sample;
  passing the incident beam to an illumination aperture that include at least a first area and a second area, the first area being arranged to block a blocked spatial portion of the incident beam and the second area being arranged to transmit a transmitted spatial portion of the incident beam towards the sample;
  directing an output beam from the sample towards a detector, the output beam comprising a specular portion and a scattered light portion; and
  passing the output beam to a complex Fourier filter positioned within a Fourier plane of the sample, wherein the complex Fourier filter has at least a first area and a second area that vary in material composition and/or thickness, wherein the relative material compositions and thickness of the first and second area are selected so as to alter a phase of the specular portions of the output beam relative to the scattered portions of the output beam so as to enhance contrast between the scattered and specular light portions of the output beam.

38. A method as recited in claim 37, wherein the output beam is transmitted through the sample.

39. A method as recited in claim 37, wherein the output beam is both reflected from and transmitted through the sample.

40. A method as recited in claim 37, wherein the output beam is both reflected and scattered from the sample.

41. A method as recited in claim 37, wherein the illumination aperture is in the form of a plurality of illumination sources which are configurable to be selectively directed onto a first plurality of ends of a plurality optical fibers that are arranged to output the incident beam in the form of a plurality of incident beams from a second plurality of ends of the fibers, wherein the fibers are coupled with a fiber modulator which is operable to substantially eliminate the speckle noise of the incident beams, the method further comprising selectively directing the incident sources onto the first optical fiber ends.

42. An apparatus as recited in claim 1, wherein the relative material compositions and thickness of the first and second area are further selected so as to alter an amplitude of the specular portions of the output beam relative to the scattered portions of the output beam so as to enhance contrast between the scattered and specular light portions of the output beam.

* * * * *